United States Patent
Zheng et al.

(10) Patent No.: US 7,018,980 B2
(45) Date of Patent: Mar. 28, 2006

(54) METHOD FOR PREPARATION OF ORALLY ADMINISTRATED INSULIN FORMULATION

(75) Inventors: Changxue Zheng, Beijing (CN); Mingxing Duan, Beijing (CN); Hong Ma, Beijing (CN); Housheng Zhong, Beijing (CN)

(73) Assignees: Tsinghua University, Beijing (CN); Fosse Bio-Engineering Development, Ltd., Hong Kong (CN)

( * ) Notice: Subject to any disclaimer, the term of this patent is extended or adjusted under 35 U.S.C. 154(b) by 0 days.

(21) Appl. No.: 10/474,474

(22) PCT Filed: Apr. 12, 2002

(86) PCT No.: PCT/CN02/00258

§ 371 (c)(1),
(2), (4) Date: Oct. 8, 2003

(87) PCT Pub. No.: WO02/085408

PCT Pub. Date: Oct. 31, 2002

(65) Prior Publication Data

US 2004/0097410 A1    May 20, 2004

(30) Foreign Application Priority Data

Apr. 20, 2001   (CN)  ............... 01115327 A

(51) Int. Cl.
*A61K 9/107* (2006.01)
*A61K 38/28* (2006.01)
*A61K 47/14* (2006.01)

(52) U.S. Cl. ............... 514/4; 514/3; 514/938
(58) Field of Classification Search .......... 514/3, 514/4, 938, 939, 940, 941, 942, 943; 530/303, 530/304, 305; 424/450
See application file for complete search history.

(56) References Cited

U.S. PATENT DOCUMENTS

| | | | | |
|---|---|---|---|---|
| 5,824,638 | A | * 10/1998 | Burnside et al. | ............... 514/3 |
| 6,258,377 | B1 | 7/2001 | New et al. | ................... 424/450 |
| 6,368,619 | B1 | 4/2002 | New et al. | ................... 424/450 |
| 2003/0166508 | A1* | 9/2003 | Zhang | ............................ 514/3 |

FOREIGN PATENT DOCUMENTS

WO    WO 94/08605    4/1994

* cited by examiner

*Primary Examiner*—Jeffrey Edwin Russel
(74) *Attorney, Agent, or Firm*—Armstrong, Kratz, Quintos, Hanson & Brooks, LLP

(57) ABSTRACT

The invention relates to the method for preparation of orally administrated insulin oil formulation comprising: dissolving an amount of insulin in an acidic aqueous buffer(A); adding A to liquid surfactant, the HLB value of which is between 10 and 20, with agitation to form a homogeneous solution(B); adding B to an oil, the HLB value of which is between 0 and 10, with agitation to form oil formulation. This invention has a simple process with low cost. After orally administrated, the formulation prepared with the process of the invention can resist the gastrointestinal degradation by digestive enzymes, and is easily absorbed for hypoglycemic effect.

6 Claims, 1 Drawing Sheet

METHOD FOR PREPARATION OF ORALLY ADMINISTRATED INSULIN FORMULATION

FIELD OF THE INVENTION

The present invention relates to the preparation of biochemical drug, in particularly relates to the new process for preparation of orally administrated peptide or protein drug.

BACKGROUND OF THE INVENTION

Many biochemical drugs, such as insulin, growth hormone, calcitonin, thrombolytic enzyme can only be administrated by injection. The patients have to suffer from the pain and discommodiousness for daily injection, even 34 injections per day of the drug like insulin, so it is desired to develop oral route of these drugs. Great benefit of economic and societal would be arisen for the breakthrough in this study. As estimated by "New Scientists" of America, the economic benefit brought with the success of this study could be up to six billion dollars per year. However, due to the intestinal proteolytic degradation and the poor penetration into the blood stream, the bioavailabilities of these biochemical drugs after direct orally administrated are lower than 0.5 percent. To overcome the disadvantages, liposome is used in some studies to enwrap insulin for the resistant of intestinal proteolytic degradation, but it's absorptivity is too low to achieve approving pharmacological effect. The insulin nanoparticles made of a -polyalkylcyanoacrylate are also be studied, but the experiment indicated that most of insulin are on the surface of nanoparticles instead of in the inside of hydrophobic capsule as anticipant. Therefore, although this nanoparticles can resist the intestinal proteolytic degradation in a certain extent, due to individual differences, it can not be used as a viable drug formulation. It is also studied to dissolve insulin in a hydrophobic solution or an oil phase for oral administration, but the process is too complex. GB patent (WO 95/13795, WO 97/34581) related to insulin oil formulation, it is needed to remove the hydrophilic solvent by circumrotate evaporation, spray evaporation even lyophilisation more than two days under a temperature of −40° C. or less and an air pressure of 0.1 millibar or less. Such technical requirements restrict the industrial scale of said process and increase the cost.

SUMMARY OF THE INVENTION

The object of the present invention is to overcome deficiency of the prior art, in particularly provides a method for preparation of orally administrated insulin oil formulation, which is simple and manageable as well as with low cost. After orally administrated, the formulation prepared with the process of the invention can resist the gastrointestinal degradation by digestive enzymes, and is easily absorbed, thus obtaining favorable hypoglycemic effect.

The invention provides a method for preparation of orally administrated insulin oil formulation which comprising:

1) dissolving an amount of insulin in an aqueous buffer, resulting in solution(A), of which the pH value is between 3 and 5, and in which the concentration of insulin is 0.1–0.5 mg/mL;

2) adding acidic solution A to a liquid nonionic surfactant or an amphiphilic ester or a mixture thereof with 10˚HLB (Hydrophile-Lipophile Balance)<20, wherein the volume ratio of solution A to that of the surfactant or the amphiphilic ester or their mixture is from 1:5 to 1:50, and then mixing at 5–30° C. with agitation to form homogeneous solution (B);

3) adding solution B to an hydrophobic emulsifier or the mixture thereof with 0<HLB<10, wherein the volume ratio of solution B to that of a hydrophobic emulsifier or their mixture is from 1:1 to 1:10, mixing this two solution at 5–30° C. with agitation to form an oil formulation(C), which is stored at 4–10'C;

4) adding an amount of antioxidant, wherein when the antioxidant is hydrophobic, the antioxidant is added to solution B during step 3), and when the antioxidant is hydrophilic, the antioxidant is added to solution A during step 2). The surfactant or amphiphilic ester or their mixture mentioned in step 2) may be one or more selected from the group consisting of decaglycerol monooleate (HLB=12.9), hexaglycerol monolaurate (HLB=13.5), decaglycerol monooctanoate (HLB=16), polyethylene glycol-8-glycerol octanoate/decanoate: (HLB=14), polyglycerol-6-dioleate (HLB=10), Tween 80 (sorbitan monooleate polyoxyalkylene) (HLB=15.4), phospholipids, glycoester, bile acid and its salt, and other biological surfactant. The agitation speed in step 2) may be 200–2000 r/min, and the agitation time is in the range of 0.5–5 hours.

The oil or hydrophobic emulsifier or their mixture mentioned in step 3) may be one or more selected from the group consisting of triglycerol octanoate/decanoate (HLB=1), glycerol octanoate/decanoate (HLB=3), glycerol oleate (HLB=3), glycerol linoleate (HLB=3), polyglycerol-3-oleate (HLB=6), polyethylene glycol-6-glycerol monooleate (HLB=4), polyethylene glycol-6-glycerol linoleate (HLB=4), Span 80 (sorbitan monooleate) (HLB=4.3), polyethylene glycol-4-glycerol octanoate/decanoate (HLB=5). The agitation temperature in step 3) is in the range of 5–30° C., the agitation speed is in the range of 200–2000 r/min, and the agitation time is in the range of 0.5–5 hours.

The amount of the antioxidant added may be 0.01–0.1% (volume ratio) relative to that of the final solution. The examples of the antioxidant are Vitamin E, Vitamin C, cysteine, gallate, tertiary butyl-hydroquinone.

The obtained oil formulation can be orally administrated directly, or enveloped into capsule (soft capsule or capsule with liquid inclusion), and can also be mixed with some kind of pharmaceutically acceptable solid excipients such as amylum, dextrine, ethylane cellulose, monostearate, in order to form troche or capsule with solid particle inclusion.

The present invention can also be used in preparation of other peptide or protein oil formulation.

The method of the invention is simple and manageable and with low cost. The dispersants and oils used in the invention are low toxicity and safety for oral administration. Insulin is even dissolved in oil phase to form a transparent insulin oil formulation. It was indicated by experiment in vitro that the formulation prepared with the process of the invention could be emulsified in the solution the pH value of which could be from 2 to 11, and the insulin are still in the oil phase instead of into the aqueous phase. After orally administrated, thus, the formulation prepared with the process of the invention can resist the gastrointestinal degradation by digestive enzymes, and is easily absorbed, thus obtaining favorable hypoglycemic effect.

EXAMPLES

Example 1

Figure 1:
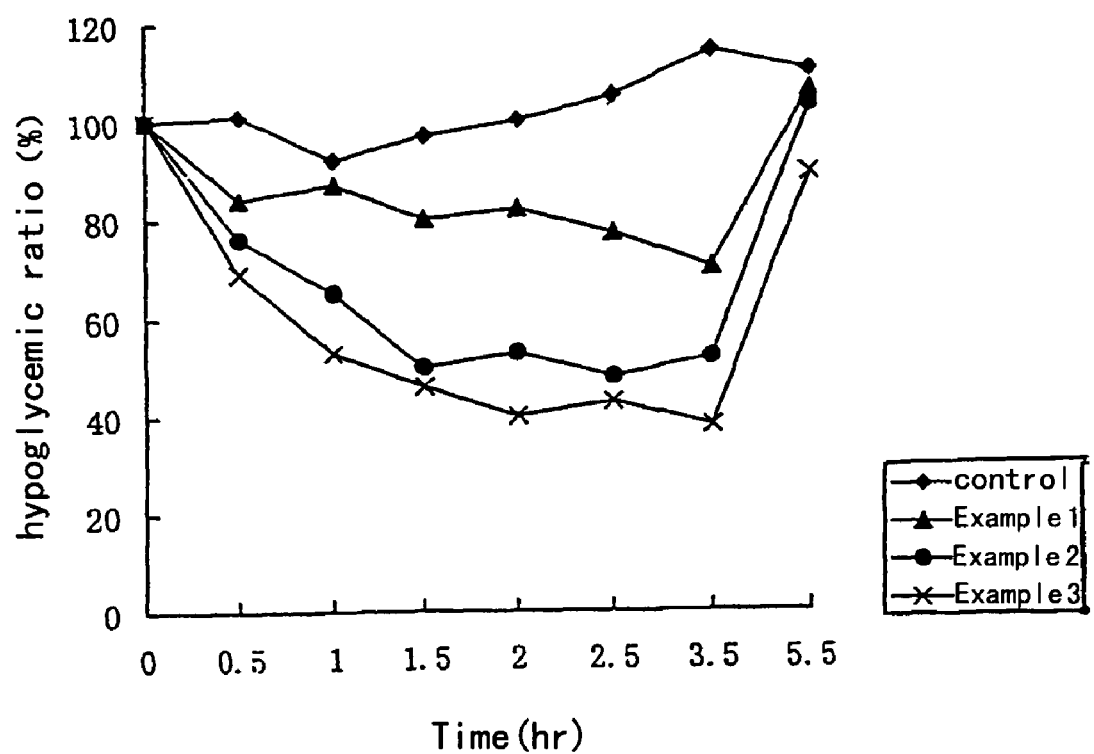
FIG. 1 is the curve of hypoglycemic effect in diabetic rats after orally administrated the insulin oil formulation prepared by the process of the invention.

1. 0.5 g of insulin was dissolved in 5 ml of buffer with the pH value of 4, resulting in a solution (A).
2. 2 ml of Tween 80 and 23 ml of decaglycerol monooctanoate were mixed totally, then solution A was added under agitation with the agitation speed of 800 r/min, the agitation period of 2 hours and the temperature of 20° C., obtaining in solution (B).
3. Solution B was added to 70 mL of glycerol oleate under agitation to form solution(C) of 100 ml total volume with the agitation speed of 800 r/min, the period of 3 hours and the temperature of 20° C.
4. 60 u l of propyl gallate was dissolved in solution C, then stored in the icebox for use.

Example 2

1. 1 g of insulin and 50 mg of Vitamin C were added to 5 ml of buffer with the pH 25 value of 4 for dissolving, and obtaining solution A.
2. Solution A was added to 40 ml of polyethylene glycol-8-glycerol octanoate/decanoate under agitation to form solution (B) of 45 ml total volume with the agitation speed of 1500 r/min, the agitation period of 2 hours and the temperature of 24"C. 30
3. 27.5 ml of polyglycerol-3-oleate and 27.5 ml of polyethylene glycol-6-glycerol monooleate were mixed, then solution B was added under agitation with an agitation speed of 1500 r/min, the agitation period of 2 hours and the temperature of 24° C. to form a solution (C), which was stored in the icebox for use.

Example 3

1. 0.8g of insulin was dissolved in 4 ml of buffer with the pH value of 4, resulting in a solution (A).
2. Solution A was added to 20 mL of polyethylene glycol-8-glycerol octanoate/decanoate to form a solution (B) of 24 mL total volume under agitation with the agitation speed of 500 r/min, the agitation period of 2.5 and the temperature of 18° C.
3. Solution B was added to 76 mL of polyglycerol-3-oleate to form a solution(C) of 100 ml total volume under agitation with the agitation speed of 500 r/min, the agitation period of 3 hours and the temperature of 18° C.
4. 80 n l of vitamin E was added to solution C, the resulting mixture was mixed totally, then stored in the icebox for use.

Animal experiments were done for the insulin oil formulation prepared by the process of the examples. Hypoglycemic effect in diabetic rats (n=10) after orally administrated the insulin oil formulation (25 IU/kg) was showed as FIG. 1.

The invention claimed is:

1. A method for preparation of orally administrated insulin formulation, comprising:
   1) dissolving an amount of insulin in an aqueous buffer, resulting in solution A, of which the pH value is between 3 and 5, and in which the concentration of insulin is 0.1–0.5 mg/mL;
   2) adding acidic solution A to a liquid nonionic surfactant or an amphiphilic ester or a mixture thereof with 10<HLB<20, wherein the volume ratio of solution A to that of the surfactant or the amphiphilic ester or their mixture is from 1:5 to 1:50, and then mixing at 5–30° C. with agitation to form homogeneous solution B;
   3) adding solution B to an hydrophobic emulsifier with 0<HLB<10, wherein the volume ratio of solution B to that of the hydrophobic emulsifier is from 1:1 to 1:10, and then mixing at 5–30° C. with agitation to form formulation C, which is stored at 4–10° C.;
   4) adding an amount of antioxidant, wherein when the antioxidant is hydrophobic, the antioxidant is added to solution B during step 3), and when the antioxidant is hydrophilic, the antioxidant is added to solution A during step 2);
   wherein the formulation does not include an oil.

2. The method of claim 1, wherein the surfactant or amphiphilic ester or their mixture mentioned in step 2) is one or more selected from the group consisting of decaglycerol monooleate, hexaglycerol monolaurate, decaglycerol monooctanoate, polyethylene glycol-8-glycerol octanoate/decanoate, polyglycerol-6-dioleate, sorbitan monooleate polyoxyalkylene (20), phospholipids, glycoester and bile acid or its salt as biological surfactant.

3. The method of claim 1, wherein the agitation speed in step 2) is in the range of 200–2000 r/min, and the agitation time is in the range of 0.5–5 hours.

4. The method of claim 1, wherein the hydrophobic emulsifier mentioned in step 3) is one or more selected from the group consisting of triglycerol octanoate/decanoate, glycerol octanoate/decanoate, glycerol oleate, glycerol linoleate, polyglycerol-3-oleate, polyethylene glycol-6-glycerol monooleate, polyethylene glycol-6-glycerol linoleate, sorbitan monooleate, and polyethylene glycol-4-glycerol octanoate/decanoate.

5. The method of claim 1, wherein the agitation temperature in step 3) is in the range of 5–30° C., the agitation speed is in the range of 200–2000 r/min and the agitation time is in the range of 0.5–5 hours.

6. The method of claim 1, wherein the amount of the antioxidant added is in the range of 0.01–0.1% by volume of the final solution, and said antioxidant comprises Vitamin E, Vitamin C, cysteine, gallate, or tertiary-butyl hydroquinone.

* * * * *